(12) United States Patent
Takeuchi et al.

(10) Patent No.: US 9,870,608 B2
(45) Date of Patent: Jan. 16, 2018

(54) GAMMA CAMERA, SPECT DEVICE, PET DEVICE, AND METHOD FOR GENERATING MEASURED GAMMA RAY IMAGES

(71) Applicant: Hitachi, Ltd., Tokyo (JP)

(72) Inventors: Wataru Takeuchi, Tokyo (JP); Atsuro Suzuki, Tokyo (JP); Yuichi Morimoto, Tokyo (JP); Isao Takahashi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 362 days.

(21) Appl. No.: 14/767,037

(22) PCT Filed: Feb. 13, 2014

(86) PCT No.: PCT/JP2014/053239
§ 371 (c)(1),
(2) Date: Aug. 11, 2015

(87) PCT Pub. No.: WO2014/148154
PCT Pub. Date: Sep. 25, 2014

(65) Prior Publication Data
US 2015/0379699 A1 Dec. 31, 2015

(30) Foreign Application Priority Data
Mar. 21, 2013 (JP) .................. 2013-057814

(51) Int. Cl.
*G06T 5/50* (2006.01)
*A61B 6/00* (2006.01)
(Continued)

(52) U.S. Cl.
CPC .............. *G06T 5/50* (2013.01); *A61B 6/482* (2013.01); *G01T 1/1647* (2013.01);
(Continued)

(58) Field of Classification Search
CPC ................................. A61B 6/482; A61B 6/483
See application file for complete search history.

(56) References Cited

U.S. PATENT DOCUMENTS

| | | | | |
|---|---|---|---|---|
| 5,633,500 A | * | 5/1997 | Morgan | G01T 1/1642 250/363.07 |
| 6,175,118 B1 | * | 1/2001 | Takayama | G01T 1/1642 250/363.07 |
| 7,470,897 B2 | * | 12/2008 | Takayama | G01T 1/1663 250/252.1 |

FOREIGN PATENT DOCUMENTS

JP 5-087933 A 4/1993

OTHER PUBLICATIONS

Scatter and crosstalk correction for simultaneous dual-isotope imaging.
(Continued)

*Primary Examiner* — Kenneth J Malkowski
(74) *Attorney, Agent, or Firm* — Mattingly & Malur, PC

(57) ABSTRACT

A unit (33) for generating count images for separate energy windows generates main measured count images and auxiliary measured count images on the basis of gamma ray (6) count information measured by a detector head (10). A main measurement window direct ray count rate estimation unit (42) estimates a count rate for direct gamma rays in a main measurement energy window, doing so by subtracting a scattered gamma ray count rate for an auxiliary measurement energy window, which has been estimated from an auxiliary measured count image and detector response data by an auxiliary measurement window scattered ray count rate estimation unit (41), from the main measured count image.

10 Claims, 12 Drawing Sheets

(51) Int. Cl.
    *G01T 1/164*     (2006.01)
    *G06T 7/00*     (2017.01)
    *H04N 5/232*     (2006.01)

(52) U.S. Cl.
    CPC ....... *G06T 7/0012* (2013.01); *H04N 5/23293* (2013.01); *G06T 2207/10104* (2013.01); *G06T 2207/10108* (2013.01)

(56) References Cited

OTHER PUBLICATIONS

Karin Knesaurek et al., Enhanced cross-talk correction technique for simultaneous dual-isotope imaging: A Tl-201/Tc-99m myocardial perfusion SPECT dog study, Med. Phys., Dec. 1997, 24(12), pp. 1914-1923.

Krzysztof Kacperski et al., Iterative deconvolution of simultaneous 99m-Tc and 201Tl projection data measured on a CdZnTe-based cardiac SPECT scanner, Physics in Medicine and Biology, 56, 2011, pp. 1397-414.

Yong Du et al., Model-based crosstalk compensation for simultaneous 99mTc/123I dual-isotope brain Spect imaging, Med. Phys. 34(9), Sep. 2007, pp. 3530-3543.

International Search Report of PCT/JP2014/053239.

\* cited by examiner

GAMMA CAMERA, SPECT DEVICE, PET DEVICE, AND METHOD FOR GENERATING MEASURED GAMMA RAY IMAGES

TECHNICAL FIELD

The present invention relates to a gamma camera, a SPECT (single photon emission computed tomography or single photon emission tomography) device, a PET (positron emission tomography) device, and a method for generating a measured gamma-ray image.

BACKGROUND ART

In the conventional cases of removing the scattered gamma-ray noise in a gamma camera, a main measurement energy window and two subsidiary measurement energy windows are set in an energy spectrum obtained by measurement, the scattered gamma-ray noise in the main measurement energy window is estimated on the basis of scattered gamma-ray noise measured in the two subsidiary measurement energy windows, and the estimated scattered gamma-ray noise is removed from the amount of the gamma-rays measured in the main measurement energy window. (See, for example, Patent Literature 1.)

The above manner of estimation and removal of the scattered gamma-ray noise is often called the TEW (triple energy window) technique. In this specification, the TEW technique is explained in detail in connection with and in comparison with the embodiment.

CITATION LIST

Patent Literatures

Patent Literature 1: Japanese Patent Laid-open No. 1993-087933 (H05-087933)

SUMMARY OF INVENTION

Technical Problem

Incidentally, in pixel-type gamma-ray detectors in each of which a number of small gamma-ray detector elements are arrayed, the energy of the gamma-rays is frequently measured lower even when the gamma-rays are primary gamma-rays, which are desired to be measured in the main measurement energy window, because of the K-escape (in which K characteristic X-rays are emitted from the gamma-ray detector elements at the respective pixels), the scattering of gamma-rays in the detector, and the like. That is, measurement signals of the primary gamma-rays are mixed into the subsidiary measurement energy windows, which are supposed to mainly include scattered components. Therefore, according to the TEW technique, the scattered gamma-ray noise is excessively estimated, and is excessively removed from the measured gamma-ray image, so that other noise occurs in the measured gamma-ray image.

In view of above, the object of the present invention is to provide a gamma camera, a SPECT device, a PET device, and a method for generating a measured gamma-ray image which enable improvement in clearness of the gamma-ray image by appropriately estimating and removing the amount of noise caused by scattered gamma-rays.

Solution to Problem

The gamma camera according to the present invention includes a pixel-type gamma-ray detector and an information processing device, which includes: a storage device which stores in advance, as detector-response data, energy spectra which are obtained when gamma-rays emitted from one or more objects to be measured are incident without being scattered; and an image display device. The gamma camera is characterized in that the information processing device includes: a first processor which generates a main-measurement count image and a subsidiary-measurement count image on the basis of integrated counts which are respectively measured by a main measurement energy window and a subsidiary measurement energy window, where the main measurement energy window is set for gamma-rays emitted from an object to be measured, and the subsidiary measurement energy window is different from the main measurement energy window; a second processor which estimates an integrated count of primary gamma-rays included in the subsidiary measurement energy window on the basis of the detector-response data and the main-measurement count image, and estimates an integrated count of scattered gamma-rays included in the subsidiary-measurement count image by subtracting the estimated integrated count of primary gamma-rays included in the subsidiary measurement energy window from the subsidiary-measurement count image; a third processor which estimates an integrated count of primary gamma-rays included in the main measurement energy window, on the basis of the integrated count of scattered gamma-rays included in the subsidiary measurement energy window, which is estimated by the second processor; and a fourth processor which generates a gamma-ray measurement image on the basis of the integrated count of primary gamma-rays estimated by the third processing, and displays the gamma-ray measurement image on the image display device.

Advantageous Effect of Invention

According to the present invention, it is possible to provide a gamma camera, a SPECT device, a PET device, and a method for generating a measured gamma-ray image which enable improvement in clearness of the gamma-ray image by appropriately estimating and removing the amount of noise caused by scattered gamma-rays.

DESCRIPTION OF EMBODIMENTS

Hereinbelow, the embodiments of the present invention are explained in detail with reference to the accompanying drawings.

Generally, in gamma cameras, it is impossible to avoid scattering of gamma-rays by substances located between the detector and a gamma-ray source as an object to be measured and by the detector system per se. Therefore, the scattered gamma-rays are mixed into the measurement data obtained by the gamma cameras. In addition, in the case where a plurality of different gamma-rays having different energies are included in the object to be measured, the gamma-rays having relatively high energies lose part of the energies, and are mixed into regions of the energy spectrum corresponding to the gamma-rays having relatively low energies.

In the embodiments, a method for estimating the noise caused by the scattered gamma-rays as above is explained by taking as examples a gamma camera, a SPECT device, and a PET device, which are nuclear medicine detector devices. However, the following explanations on the embodiments can be applied to not only the nuclear medicine detector devices but also common gamma cameras.

The radionuclides in the test agents used with the gamma cameras, SPECT devices, and the like in the field of nuclear medicine include, for example, $^{99m}$Tc (141 keV), $^{123}$I (159 keV, 529 keV), $^{201}$Tl (70.8 keV, 135 keV, 167 keV), $^{111}$In (171 keV, 245 keV), and $^{67}$Ga (93.3 keV, 185 keV, 300 keV). In addition, in the brain function test by SPECT, agents labeled by $^{99m}$Tc or $^{123}$I are used in many cases for estimation of the cerebral blood flow, imaging of a receptor of a neurotransmitter (e.g., for searching for epileptic focus), and the like.

However, since the gamma-ray energies of $^{99m}$Tc and $^{123}$I are close, separation of the energy peaks of the respective radionuclides is difficult. Therefore, simultaneous multi-radionuclide imaging is not commonly performed.

The gamma-rays emitted by the above test agents interact with substances (such as the subject and the collimator) located between the gamma-ray source and the detector, and are therefore absorbed (or attenuated) or scattered. The scattered gamma-rays are deflected and become noise having lower energy than the primary gamma-rays because the gamma-rays lose their energy by the scattering.

Comparison Example

Figure 1:
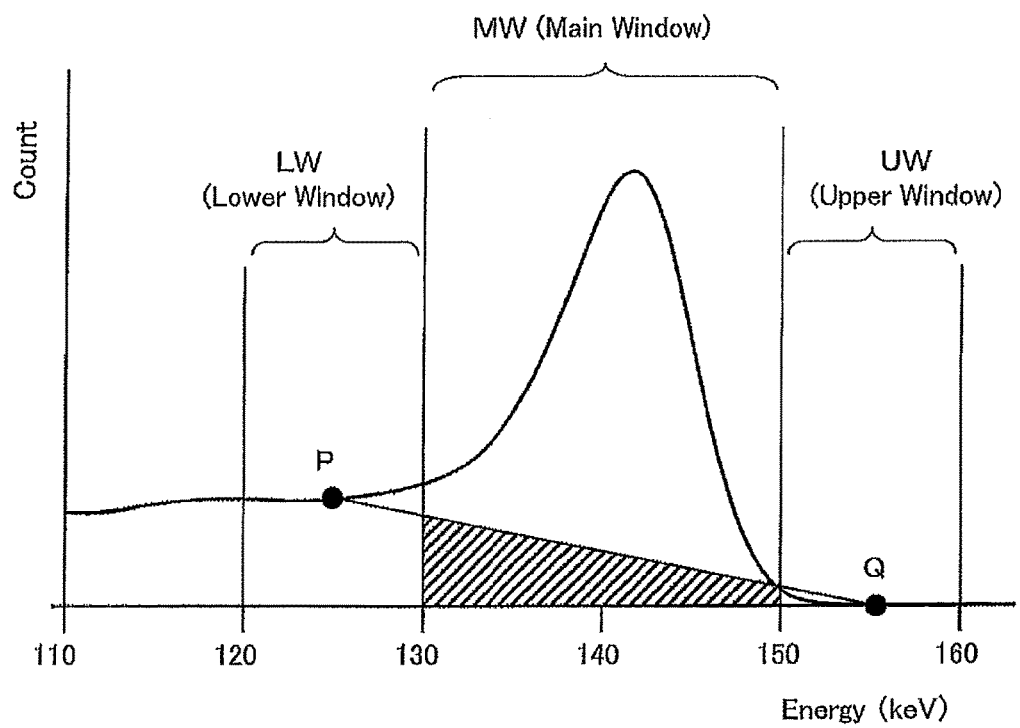
FIG. 1 is a schematic view of a method for estimating scattered gamma-ray noise by the TEW technique.

Hereinbelow, the TEW technique, which has been commonly used, is explained as a comparison example of a manner of estimating the noise caused by the scattered gamma-rays. FIG. 1 is a schematic view of a method for estimating scattered gamma-ray noise by the TEW technique.

As illustrated in FIG. 1, in the TEW technique, a main measurement energy window (main window) is set on an energy spectrum produced on the basis of the energies detected by each gamma-ray detector element constituting a gamma camera, such that the main window includes the peak energy range.

(Hereinafter, the main window may be referred to as the MW.) In addition, a first subsidiary measurement energy window (lower window) is set in a range adjacent to the MW on the lower energy side, and a second subsidiary measurement energy window (upper window) is set in a range adjacent to the MW on the higher energy side. (Hereinafter, the lower window may be referred to as the LW, and the upper window may be referred to as the UW.)

In the above settings, primary gamma-rays from the gamma-ray source are largely detected in the MW, and scattered gamma-rays are largely detected in the LW. On the other hand, neither of the primary gamma-rays and the scattered gamma-rays are detected in the UW so largely. Therefore, the average values of the amounts of gamma-rays detected in the LW and the UW are respectively regarded as the average noise levels of the scattered gamma-rays in the LW and the UW, and the amount of noise of scattered gamma-rays in the MW is estimated on the basis of the noise levels of the scattered gamma-rays in both of the LW and the UW.

In the estimation of the noise amount according to the TEW technique, a point P is set at the average noise level in the LW in the center of the LW in the energy spectrum of FIG. 1, a point Q is set at the average noise level in the UW in the center of the UW, and the straight line PQ is regarded as a scattered-gamma-ray noise estimation line for determining the noise amount of the scattered gamma-rays in the MW. That is, the hatched region under the straight line PQ (i.e., the scattered-gamma-ray noise estimation line) having a trapezoidal shape corresponds to the estimated noise amount of scattered gamma-rays.

Therefore, when the hatched trapezoidal region under the straight line PQ is subtracted from the peak area of the energy spectrum (which is obtained before), the noise caused by the scattered gamma-rays is removed, so that the integrated count of the primary gamma-rays in the MW can be obtained. In this description, the abscissa of each energy spectrum indicates the energy, the ordinate indicates the count, and the value of the count integrated in an interval of the energy is referred to as an integrated count.

Figure 2:
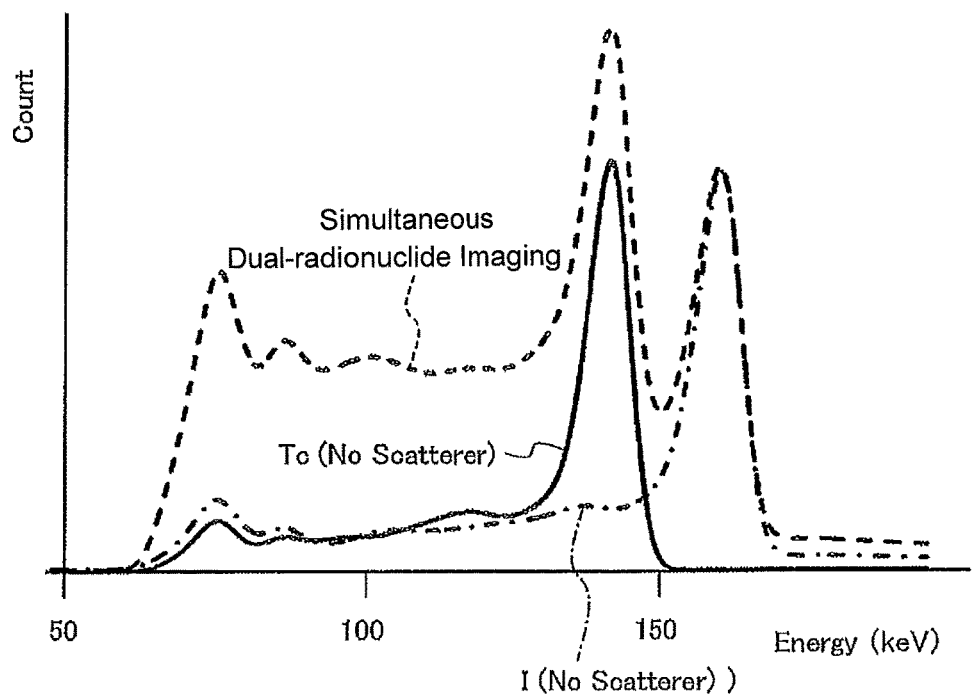
FIG. 2 is a graph illustrating an example of an energy spectrum in simultaneous dual-radionuclide imaging.

FIG. 2 is a graph illustrating an example of an energy spectrum in simultaneous dual-radionuclide imaging. In FIG. 2, the dashed curve indicates an example of an energy spectrum which is obtained when simultaneous dual-radionuclide imaging in which $^{99m}$Tc and $^{123}$I are mixed is performed. In addition, the solid curve and the dot-and-dash curve respectively indicate examples of energy spectra of $^{99m}$Tc and $^{123}$I as single-radionuclide gamma-ray sources, where the energy spectra are measured under conditions in which almost no scattered gamma-rays occur.

The overlapping of energy spectra in the simultaneous dual-radionuclide imaging has mainly the following two causes. The first cause is that the gamma-rays originally emitted from $^{123}$I, which have relatively high energy, lose energy due to scattering, so that the gamma-rays having the reduced energy are mixed into the energy spectrum of $^{99m}$Tc in a relatively low energy range. The second cause is that the energy resolution, on the measurement side, of even the primary gamma-rays is insufficient, so that the detected energy peaks overlap. The above phenomenon is called crosstalk.

As described above, in the simultaneous dual-radionuclide imaging, even in the case where no scatterer exists, signals caused by $^{123}$I are mixed into the measurement energy window for $^{99m}$Tc due to crosstalk. Since the crosstalk is caused by energy reduction of the primary gamma-rays during the detection process, the true distribution of the test agent is reflected in the crosstalk. However, since the scattered gamma-rays are gamma-rays which have lost part of energy and been deflected in the subject, the scattered gamma-rays widely spread, and therefore do not give much structural information on the subject. Thus, in the simultaneous dual-radionuclide imaging, noise components having greatly different spatial distributions being caused by $^{123}$I and having greatly different spatial distributions are mixed into the LW, MW, and UW for $^{99m}$Tc. For example, crosstalk between the scattered gamma-rays originally emitted from by $^{123}$I and primary gamma-rays occurs in the LW, MW, and UW for $^{99m}$Tc.

By the way, in the pixel-type detector used in the present embodiment, signals indicating energies lower than the original gamma-ray energy are detected in unignorable proportions because of further phenomena including the K-escape in which K characteristic X-rays are emitted from the gamma-ray detector elements and the phenomenon in which gamma-rays are not entirely absorbed and are instead scattered. In this description, the above phenomena are referred to as detection energy loss.

Actually, as illustrated in FIG. 2, in the energy spectrum in the case where no scatterer exists, gamma-rays are detected in the wide range on the lower energy side of the spectrum peak of the original gamma-ray energy in spite of the absence of scattered gamma-rays. Similarly to the aforementioned crosstalk in simultaneous multi-radionuclide imaging, the detection energy loss causes part of the primary gamma-rays to have wrong energy information and be mixed into other measurement energy windows, although the primary gamma-rays are to be actually measured as true signals. Therefore, the detection energy loss is a factor deteriorating the accuracy of measurement in the case where the noise caused by scattered gamma-rays is corrected by use of multiple energy windows, not only in the simultaneous multi-radionuclide imaging and also in the single-radionuclide imaging.

Hereinbelow, a method of estimating the noise of scattered gamma-rays in consideration of the detection energy loss is explained with reference to drawings when necessary. In the following explanations, an example of single-radionuclide imaging is explained as the first embodiment, and an example of simultaneous multi-radionuclide imaging is explained as the second embodiment.

First Embodiment

Figure 3:
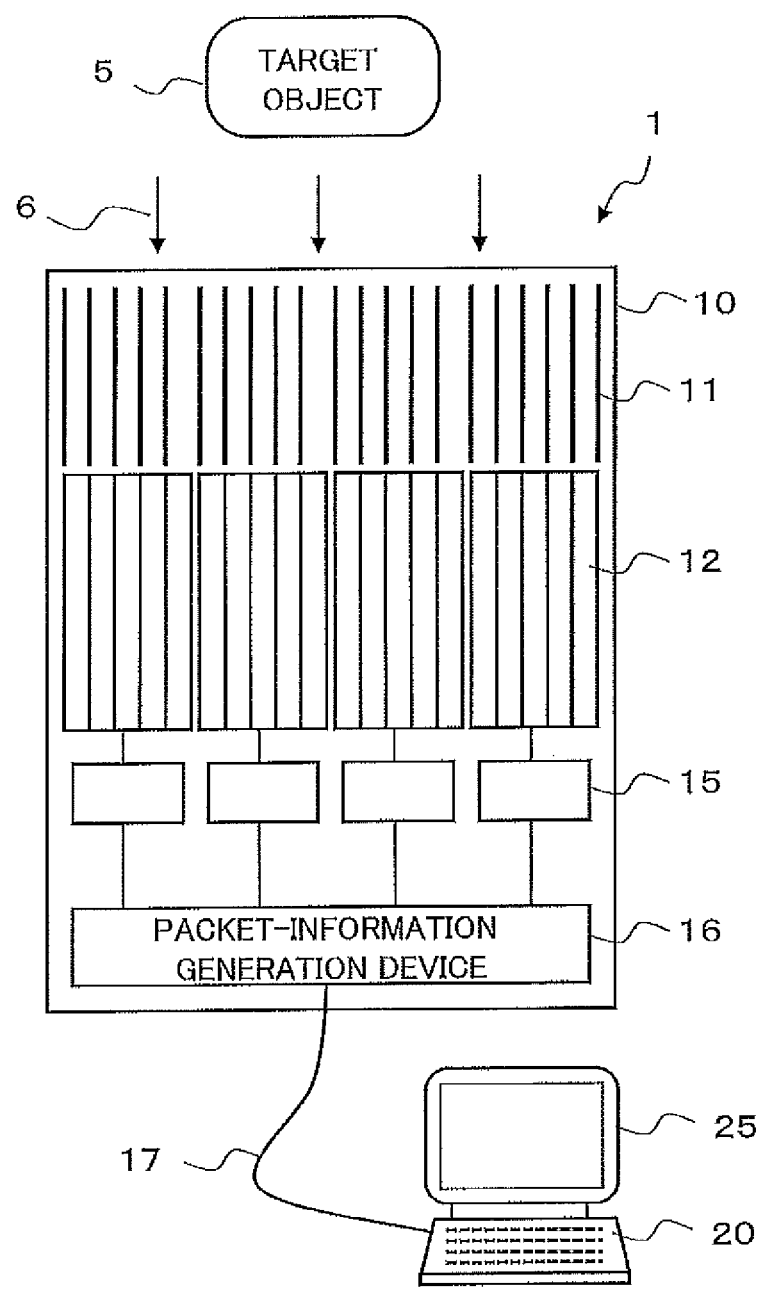
FIG. 3 is a diagram illustrating an example of a structure of a gamma camera according to a first embodiment of the present invention.

FIG. 3 is a diagram illustrating an example of a structure of a gamma camera according to the first embodiment of the present invention. As illustrated in FIG. 3, the gamma camera 1 is constituted by a detector head 10 and an information processing device 20. The detector head 10 contains a pixel-type gamma-ray detector, and the pixel-type gamma-ray detector is constituted by a number of semiconductor gamma-ray detectors 12, which are arrayed. The information processing device 20 generates a measured gamma-ray image of a target object 5 on the basis of detection signals detected by the semiconductor gamma-ray detectors 12.

The detector head 10 includes a collimator 11, a signal amplifier 15, a packet-information generation device 16, and other devices as well as the semiconductor gamma-ray detectors 12. In addition, the information processing device 20 includes an image display device 25 and other devices, and is connected to the packet-information generation device 16 in the detector head 10 through a communication cable 17.

The gamma-rays 6 emitted from the target object 5 enter the semiconductor gamma-ray detectors 12 at incident directions limited by the collimator 11. The gamma-rays 6 incident on the semiconductor gamma-ray detectors 12 generate electrons and positive holes (not shown) in the semiconductor gamma-ray detectors 12 by interaction with the semiconductor gamma-ray detectors 12. The semiconductor gamma-ray detectors 12 measure the electrons and positive holes as electric signals between positive and negative electrodes (not shown). In addition, the measured electric signals are amplified by the signal amplifier 15, converted into digital information by an A/D (analog to digital) converter (not shown), and transmitted to the packet-information generation device 16. For each digitized detection signal, the packet-information generation device 16 packetizes, as the gamma-ray detection data, the detection time, the detected energy, the detection position or the number indicating the detector which performs the detection. Then, the packet-information generation device 16 transfers the packet to the information processing device 20.

In the present embodiment, it is assumed that the collimator 11 is a parallel hole collimator, and the semiconductor gamma-ray detectors 12 is a type using cadmium telluride (CdTe). However, in the gamma camera 1 according to the present embodiment, the type of the collimator 11 and the material of which the semiconductor gamma-ray detectors 12 are formed are not specifically limited. For example, the collimator 11 may be a pinhole collimator or a fan-beam collimator. In addition, the semiconductor gamma-ray detectors 12 may be formed of thallium bromide (TlBr), cadmium zinc telluride (CZT), or the like.

Figure 4:
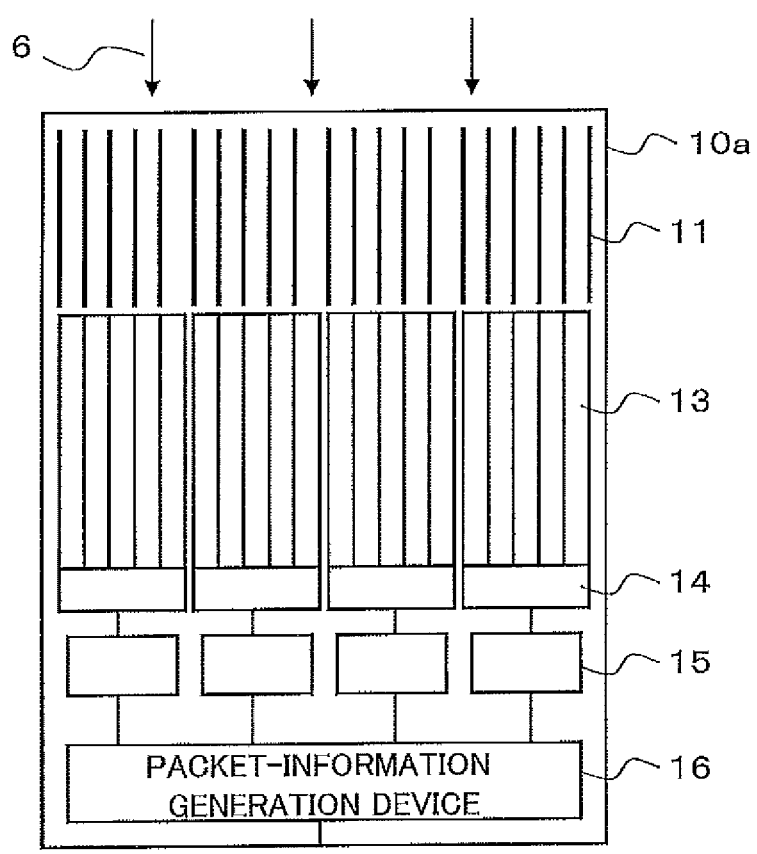
FIG. 4 is a diagram illustrating an example of a structure of a detector head in the case where a pixel type detector is constituted by a scintillator.

FIG. 4 is a diagram illustrating an example of a structure of the detector head in the case where the pixel type detector is constituted by a scintillator. As illustrated in FIG. 4, the detector head 10a is constituted by the collimator 11, scintillators 13, optical detectors 14, a signal amplifier 15, a packet-information generation device 16, and other components. In other words, the detector head 10a is a variation of the detector head 10 illustrated in FIG. 3 having a structure obtained by replacing the semiconductor gamma-ray detectors 12 in the detector head 10 with the scintillators 13 and the optical detectors 14.

The scintillators 13 may be formed of lanthanum bromide (LaBr$_3$) or sodium iodide (NaI). Photomultipliers, MPPCs (multi-pixel photon counters), or the like may be used as the optical detectors 14.

In the following explanations in this description, it is assumed that the structure of the detector head 10 is based on FIG. 3, and the semiconductor gamma-ray detectors 12 using cadmium telluride (CdTe) are used as detectors for the gamma-rays 6.

Figure 5:
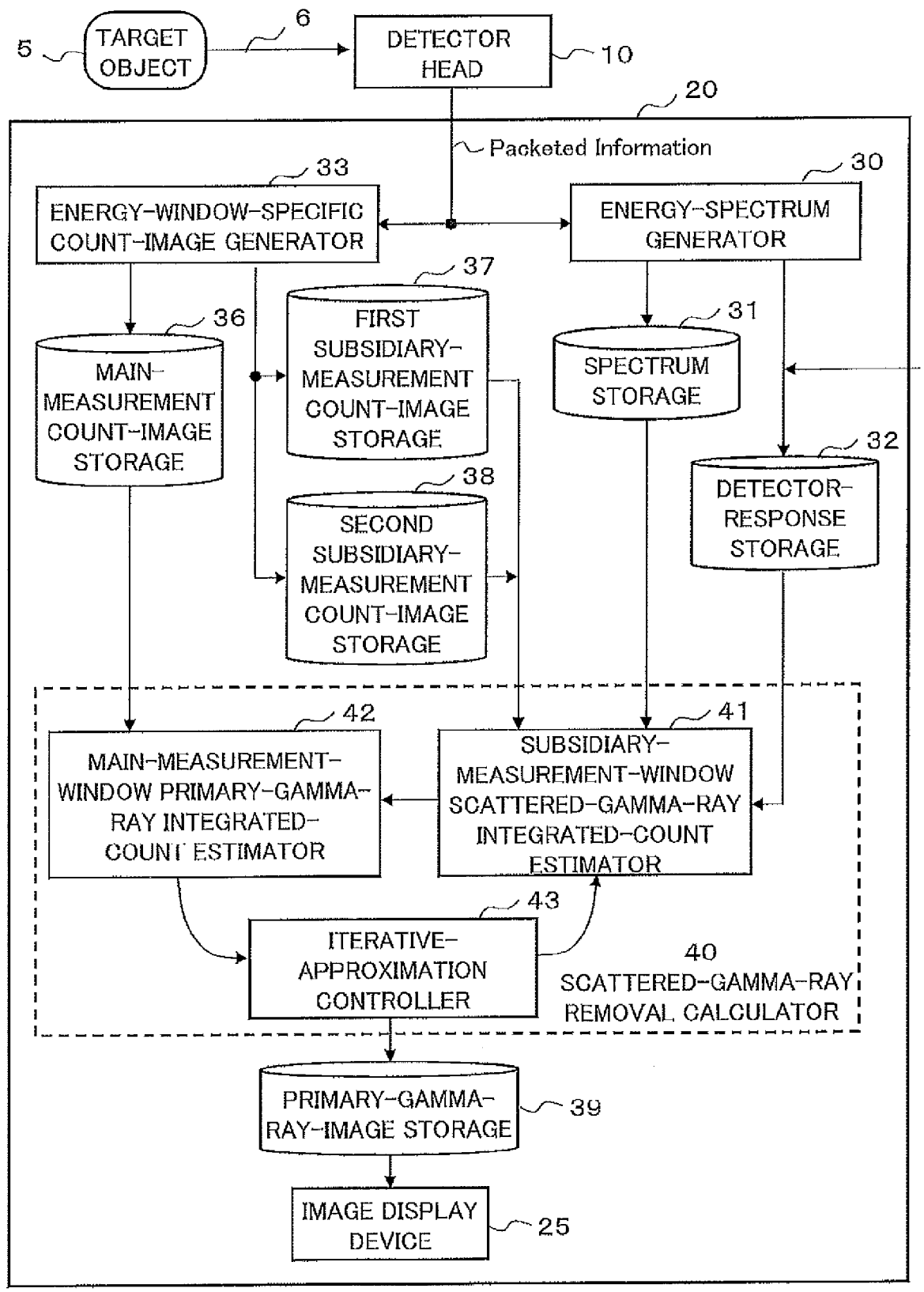
FIG. 5 is a diagram illustrating an example of a function block structure of an information processing device according to the first embodiment of the present invention.

FIG. 5 is a diagram illustrating an example of a function block structure of the information processing device 20 according to the first embodiment of the present invention. The information processing device 20 is assumed to be constituted by a computer constituted by a CPU (central processor) and a storage device (a semiconductor memory, a hard disk drive, and the like).

The information processing device 20 includes as function-realizing blocks an energy-spectrum generator 30, an energy-window-specific count-image generator 33, a scattered-gamma-ray removal calculator 40, and other functions. In addition, the information processing device 20 includes, as blocks developed on the storage device, a spectrum storage 31, a detector-response storage 32, a main-measurement count-image storage 36, a first subsidiary-measurement count-image storage 37, a second subsidiary-measurement count-image storage 38, a primary-gamma-ray-image storage 39, and other functions.

The energy-spectrum generator 30 generates an energy spectrum of detected gamma-rays by using the gamma-ray detection data included in the information packet transferred from the packet-information generation device 16 in the detector head 10, and stores the energy spectrum in the spectrum storage 31.

The energy spectra in the case where the gamma-rays 6 emitted from a radionuclide as the target object 5 are incident on the present gamma-ray detector without being scattered are stored as detector-response data in the detector-response storage 32. The detector-response data are assumed to be obtained in advance by actual measurement, simulation calculation, or the like.

The energy-window-specific count-image generator 33 sets a main measurement energy window and subsidiary measurement energy windows on the basis of the detected energy included in the information packet sent from the packet-information generation device 16, and counts the gamma-ray detection signals in each measurement energy window for each detection position, and generates a count image in each measurement energy window.

In the present embodiment, a single radionuclide of $^{99m}$Tc (141 keV) is used as the target object 5, and one main measurement energy window and two subsidiary measurement energy window are set for the energy spectra of the target object (as illustrated in FIG. 1). In FIG. 1, the MW (130 keV to 150 keV) corresponds to the main measurement energy window, and the LW (120 keV to 130 keV) and the UW (150 keV to 160 keV) respectively correspond to the first subsidiary measurement energy window and the second subsidiary measurement energy window.

The count images generated in the measurement energy windows by the energy-window-specific count-image generator 33 are respectively stored in the main-measurement count-image storage 36, the first subsidiary-measurement count-image storage 37, and the second subsidiary-measurement count image store department 38.

The scattered-gamma-ray removal calculator 40 is constituted by a subsidiary-measurement-window scattered-gamma-ray integrated-count estimator 41, a main-measurement-window primary-gamma-ray integrated-count estimator 42, and an iterative-approximation controller 43.

The subsidiary-measurement-window scattered-gamma-ray integrated-count estimator 41 estimates the primary-gamma-ray components included in the count images in the subsidiary measurement energy windows on the basis of the detector-response data stored in the detector-response storage 32 and the main-measurement count image stored in the main-measurement count-image storage 36, and estimates the count images of scattered gamma-rays in the subsidiary measurement energy windows by subtracting the estimated primary-gamma-ray components from the subsidiary-measurement count images.

The main-measurement-window primary-gamma-ray integrated-count estimator 42 estimates the scattered-gamma-ray component in the main measurement energy window by using the estimated subsidiary-measurement count images of the scattered gamma-rays, and estimates the main-measurement count image of the primary gamma-ray component by subtracting the estimated scattered-gamma-ray component from the main count image.

The iterative-approximation controller 43 controls the subsidiary-measurement-window scattered-gamma-ray integrated-count estimator 41 and the main-measurement-window primary-gamma-ray integrated-count estimator 42 such that the processing by the main-measurement-window primary-gamma-ray integrated-count estimator 42 based on a result obtained by the subsidiary-measurement-window scattered-gamma-ray integrated-count estimator 41 and the processing by the subsidiary-measurement-window scattered-gamma-ray integrated-count estimator 41 based on a result obtained by the main-measurement-window primary-gamma-ray integrated-count estimator 42 are repeatedly performed. In addition, every time the above processing is repeated, the iterative-approximation controller 43 determines whether or not a predetermined convergence condition is reached. When the convergence condition is reached, the iterative-approximation controller 43 stops the above repeated processing, stores in the primary-gamma-ray-image storage 39 the output of the main-measurement-window primary-gamma-ray integrated-count estimator 42 obtained at that time as the primary-gamma-ray image in which the noise component caused by the scattered gamma-rays are appropriately estimated and removed, and displays the primary-gamma-ray image on the image display device 25.

Next, details of the calculation process by the scattered-gamma-ray removal calculator 40 are explained by using mathematical formulas for an exemplary case in which a single radionuclide of $^{99m}$Tc is used as the target object 5.

In addition, the calculation processing explained below may be performed for each pixel value on a count image, or on the basis of the sum total or an average of the pixel values, or on the basis of the sum total or an average of pixel values in each of arbitrary areas into which the count image is divided. However, in the case where the statistical precision at each pixel on the count image is sufficient, it is appropriate to perform the calculation processing for each pixel value.

First, in the TEW technique indicated in FIG. 1, the count image $E_M$ of gamma-rays measured in the measurement energy window X is expressed by the formulas (1), where $N_T(X)$ denotes the integrated count of primary gamma-rays from the radionuclide N which is measured in the measurement energy window X, $N_S(X)$ denotes the integrated count of scattered gamma-rays from the radionuclide N which is measured in the measurement energy window X, X is the MW (main window) when X=M, X is the IW (lower window) when X=L, and X is the UW (upper window) when X=U.

Although $N_T(X)$ and $N_S(X)$ are assumed to be the integrated counts at each pixel constituting the count image Ex, no subscript indicating the pixel is attached for simplification of explanations. However, the present invention is not limited by the above manner, and the ranges in which the following calculation processing is performed are arbitrary as mentioned before.

$$E_L = N_S(L),\ E_M = N_T(M) + N_S(M),\ E_U = N_S(U) \qquad (1)$$

That is, the count image $E_L$ measured in the LW is expressed by the integrated count $N_S(L)$ of scattered gamma-rays measured in the LW among all the scattered gamma-rays from the radionuclide N as the target object 5, and the count image $E_M$ measured in the main measurement window MW is expressed by the sum of the integrated count $N_T(M)$ of the primary gamma-rays and the integrated count $N_S(M)$ of scattered gamma-rays measured in the MW, and the count image $E_U$ measured in the UW is expressed by the integrated count $N_S(U)$ of scattered gamma-rays measured in the UW. However, the integrated count $N_S(U)$ becomes zero in many cases.

In the TEW technique, the integrated count $N_S(M)$ of scattered gamma-rays mixed into the MW is estimated on the basis of the above count images $E_L$, $E_M$, and $E_U$ by approximation with a trapezoid (the hatched area) illustrated in FIG. 1. In addition, the integrated count $N_T(M)$ of the primary gamma-rays is calculated by the following formula (2).

$$N_T(M) = TEW(E_L, E_M, E_U) \qquad (2)$$
$$= E_M - (\alpha \cdot E_L + \beta \cdot E_U)$$
$$= N_T(M) + N_S(M) - (\alpha \cdot N_S(L) + \beta \cdot N_S(U))$$

where $$\alpha = \frac{c_U - c_M}{c_U - c_L} \cdot \frac{w_M}{w_L}, \beta = \frac{c_M - c_L}{c_U - c_L} \cdot \frac{w_M}{w_U}$$

In the formula (2), $W_X$ denotes the width of the measurement energy window X, and $C_X$ denotes the median of the measurement energy window X. In addition, the term $(\alpha \cdot E_L + \beta \cdot E_U)$ is the estimated integrated count of scattered gamma-rays, and corresponds to the area of the (hatched) trapezoid illustrated in FIG. 1.

By the way, in the case where the gamma-ray detector is a pixel-type detector as in the present embodiment, the aforementioned detection energy loss increases the proportion of the primary gamma-rays detected as gamma-rays having energies lower than the original gamma-ray energy. In other words, the primary gamma-rays, which are desired to be detected in the MW, are detected in the LW, and therefore the count image $E_L$ is expressed by the following formula (3).

$$E_L = N_T(L) + N_S(L) \qquad (3)$$

That is, since part of the primary gamma-rays are included in the count image $E_L$ in the LW, the count image $E_L$ becomes greater than the integrated count $N_S(L)$ of the actual scattered gamma-rays. In other words, the integrated count $N_S(M)$ of the scattered gamma-rays in the MW which is estimated as the area of the hatched trapezoid in the conventional TEW technique is overestimated, so that the integrated count $N_T(M)$ of the primary gamma-rays is excessively corrected.

Therefore, according to the present embodiment, the integrated count $N_T(L)$ of primary gamma-rays which are mixed into the LW is estimated and removed. Thus, according to the present embodiment, a probability distribution indicating what energies are measured when the primary gamma-rays originally emitted from the radionuclide as the target object are incident on the present gamma-ray detector is obtained in advance by measurement or experiment, and stored as the detector-response data in the detector-response storage 32. Such detector-response data can be obtained, for example, by measuring a point source, a thin surface source, or the like.

That is, the integrated count $N_T(L)$ of primary gamma-rays which are included in the LW can be estimated by using the detector-response data and the count image $E_M$. In addition, the integrated count $N_S(L)$ of the scattered gamma ray included in the LW is obtained by subtracting the estimated integrated count $N_T(L)$ of the primary gamma-rays included in the LW from the count image $E_L$ in the LW. Hereinafter, the method for estimating the integrated count $N_S(L)$ of the scattered gamma ray included in the LW as above is referred to as the TEW-DRC technique in distinction from the TEW technique.

Figure 6:
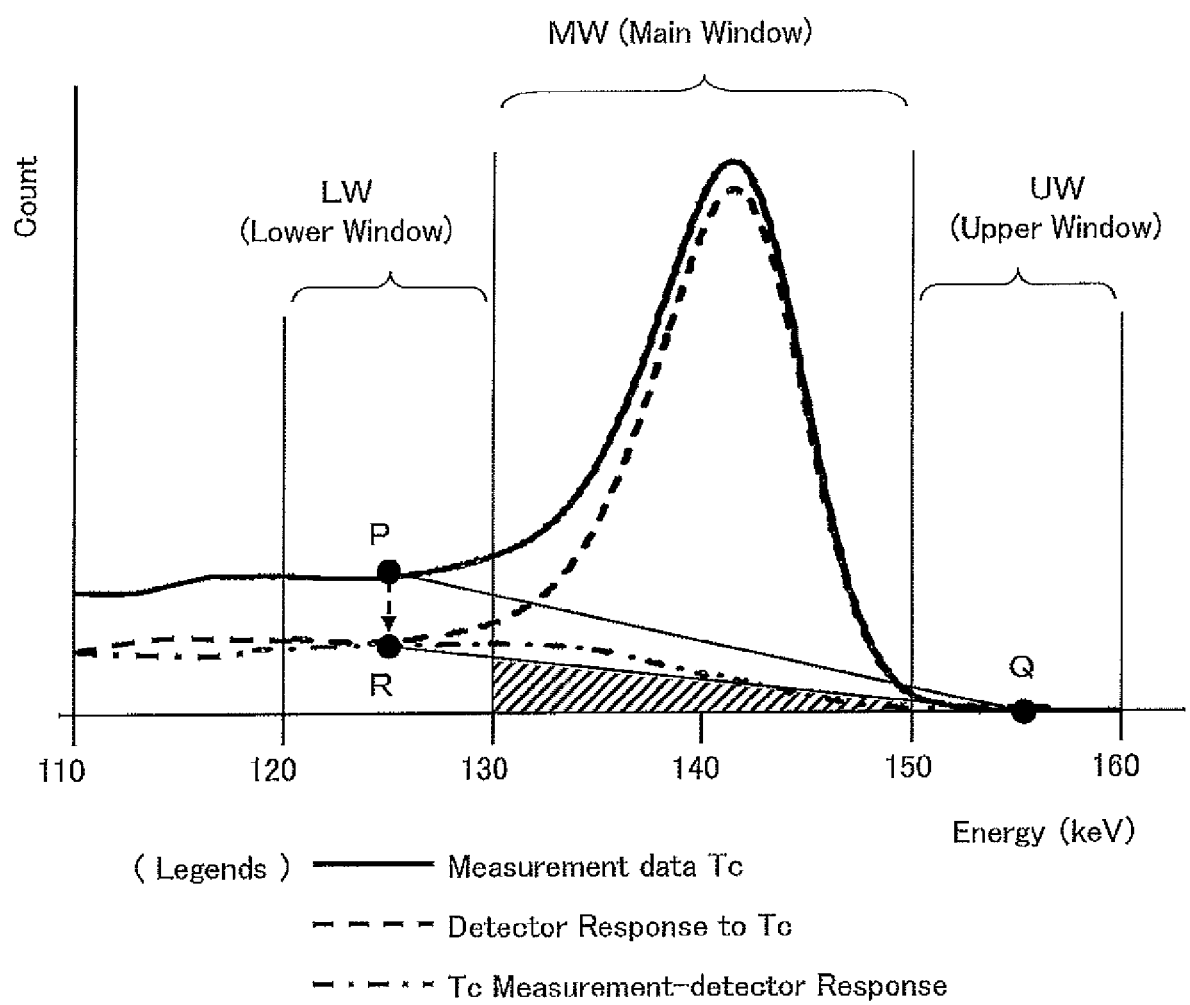
FIG. 6 is a schematic view of a method for estimating scattered gamma-ray noise by the TEW-DRC technique according to the first embodiment of the present invention.

FIG. 6 is a schematic view of the method for estimating scattered gamma-ray noise by the TEW-DRC technique according to the first embodiment of the present invention. In FIG. 6, an energy spectrum of $^{99m}Tc$ in a subject containing scatterers is indicated as Tc measurement data, and an energy spectrum of a surface source of $^{99m}Tc$ is indicated as detection response to Tc. In addition, the Tc measurement data minus the detection response to Tc is indicated as measurement-detector response, which can be regarded as the scattered-gamma-ray component in the Tc measurement data.

According to the conventional TEW technique, the scattered-gamma-ray component is estimated by use of the straight line PQ. On the other hand, according to the present embodiment (the TEW-DRC technique), the area between the straight line PQ and the straight line RQ is regarded to correspond to the primary-gamma-ray component mixed into the LW, and the area of the (hatched) trapezoid under the straight line RQ is estimated as the scattered-gamma-ray component.

Hereinbelow, the processing for estimating scattered gamma-ray noise by the TEW-DRC technique is explained by using the formulas (4) to (8). Although the integrated count $N_T(M)$ of the primary gamma-rays in the MW is required to be finally obtained by the processing, in order to apply the estimation method illustrated in FIG. 6, the integrated count $N_S(L)$ of the scattered gamma-rays is first obtained.

First, the ratio of the total integrated count $N_{DR}(L)$ of detector response in the LW to the total integrated count $N_{DR}(M)$ of detector response in the MW is defined as the detector response ratio f as indicated in the formula (4).

$$f = N_{DR}(L)/N_{DR}(M) \qquad (4)$$

Thus, the integrated count $N_T(L)$ of the primary gamma-rays included in the LW can be regarded as the product of the integrated count $N_T(M)$ of the primary gamma-rays in the MW and the detector response ratio f. Therefore, the formula (5) is derived from the formula (3).

$$N_S(L) = E_L - N_T(L) = E_L - f \cdot N_T(M) \qquad (5)$$

However, the integrated count $N_T(M)$ of the primary gamma-rays in the MW, which is on the right side of the formula (5), is the quantity required to be obtained, and is not yet known. Therefore, first, $E_L$ in the formula (2) is replaced with $N_S(L)$ to obtain the formula (6). This operation corresponds to the processing by the main-measurement-window primary-gamma-ray integrated-count estimator 42 (illustrated in FIGS. 5 and 6).

$$N_T(M) = TEW(N_S(L), E_M, E_U) \qquad (6)$$

When substitution of $N_T(M)$ obtained as above by the formula (6) into the formula (5) and substitution of $N_T(M)$ obtained by the formula (5) into the formula (6) are repeatedly performed, the recurrence formulas (7) and (8) are obtained.

$$N_{S,n}(L) = E_L - f \cdot \text{TEW}(N_{S,n-1}(L), E_M, E_U) \quad (7)$$

$$N_{T,n}(M) = \text{TEW}(N_{S,n}(L), E_M, E_U) \quad (8)$$

In the above formulas (7) and (8), n denotes the number of the repetitions. In addition, the initial value in the above recurrence formulas is $N_{S,0}(L)=E_L$.

Further, the calculation of the formula (5) or (7) corresponds to the processing by the subsidiary-measurement-window scattered-gamma-ray integrated-count estimator 41 (illustrated in FIG. 5), and the calculation of the formula (6) or (8) corresponds to the processing by the main-measurement-window primary-gamma-ray integrated-count estimator 42.

The iterative-approximation controller 43 controls the iterative calculations of the aforementioned recurrence formulas, and performs a convergence test. The convergence test can be performed, for example, by determining whether or not the difference of the calculated value of the formula (8) from the previous value falls below a predetermined threshold value. In addition, when a convergence is determined by the convergence test, the calculated value of the formula (8) at the time of the convergence determination is determined to be the integrated count of primary gamma-rays in the MW in which the integrated count of scattered gamma-rays is appropriately removed.

In the above explanations, the calculation by the main-measurement-window primary-gamma-ray integrated-count estimator 42 is performed in accordance with the TEW technique. Since the TEW technique is based on the simple calculation formulas as the formula (2), the analytic solution of the recurrence formulas of formula (7) and (8) can be obtained as indicated in the formula (9).

$$\begin{aligned} N_T(M) &= \text{TEW\_DRC}(E_L, E_M, E_U) \\ &= \text{TEW}(\lim_{n\to\infty} N_{S,n}(L), E_M, E_U) \\ &= E_M - \left( \alpha \cdot \frac{E_L - f \cdot E_M + \beta \cdot f \cdot E_U}{1 - \alpha \cdot f} + \beta \cdot E_U \right) \end{aligned} \quad (9)$$

Figure 7:
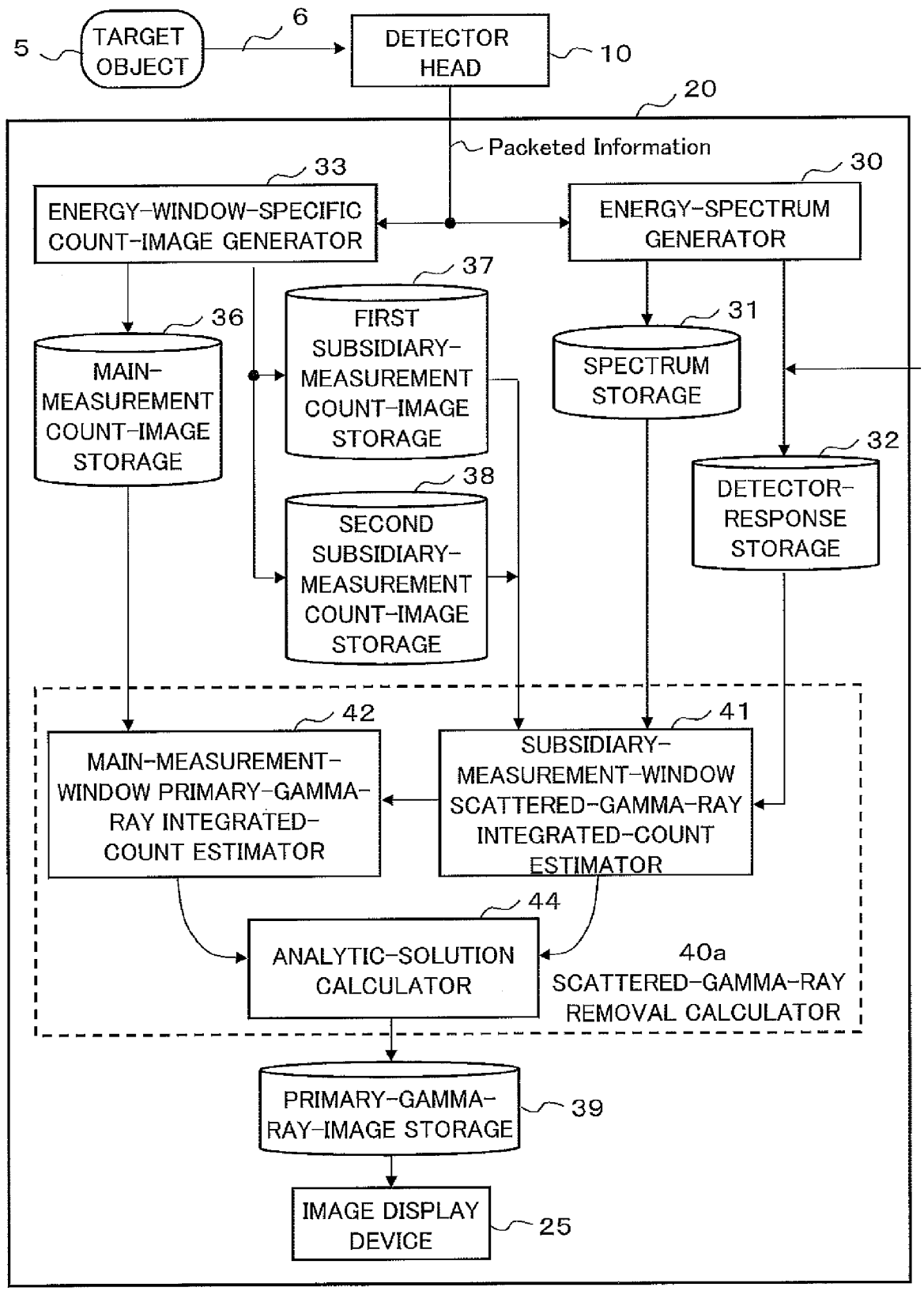
FIG. 7 is a diagram illustrating a variation of the function block structure of the information processing device according to the first embodiment of the present invention.

FIG. 7 is a diagram illustrating a variation of the function block structure of the information processing device according to the first embodiment of the present invention. The iterative-approximation controller 43 in the construction of the information processing device 20 illustrated in FIG. 5 is replaced with an analytic-solution calculator 44 in the function block structure of the information processing device 20a illustrated in FIG. 7. Thus, in the above variation, the scattered-gamma-ray removal calculator 40a is constituted by the subsidiary-measurement-window scattered-gamma-ray integrated-count estimator 41, the main-measurement-window primary-gamma-ray integrated-count estimator 42, and the analytic-solution calculator 44.

In other words, the function block structure of the information processing device 20a in the above variation is adapted for the case where the recurrence formulas (7) and (8) have an analytic solution. Therefore, the analytic-solution calculator 44 directly calculates $N_T(M)$ in accordance with the formula (9) instead of controlling the subsidiary-measurement-window scattered-gamma-ray integrated-count estimator 41 and the main-measurement-window primary-gamma-ray integrated-count estimator 42 to repeatedly perform the processing.

The explanations on the first embodiment are supplemented as follows. In the first embodiment, the TEW technique is used as the estimation method based on which the main-measurement-window primary-gamma-ray integrated-count estimator 42 performs processing, so that the mathematical expressions as the formulas (7), (8), and (9) are enabled. However, the processing by the main-measurement-window primary-gamma-ray integrated-count estimator 42 is not limited to such mathematical expressions, and instead the estimation processing by the main-measurement-window primary-gamma-ray integrated-count estimator 42 may use a neural network, a Monte Carlo simulation, or the like.

In addition, the gamma camera 1 according to the first embodiment explained above is not limited to gamma cameras for medical use, and can be used as gamma cameras for use, for example, in measurement of indoor and outdoor environmental radiation.

In the first embodiment of the present invention, the integrated count of scattered gamma-rays in the subsidiary measurement windows (LW, UW) are estimated on the basis of a result of estimation of the integrated counts of primary gamma-rays mixed into the integrated counts of gamma-rays measured in the subsidiary measurement windows (LW, UW). Therefore, the integrated count of scattered gamma-rays included in the integrated count of gamma-rays measured in the main measurement window (MW) can be estimated with high accuracy. That is, the accuracy of the estimation of the integrated count of primary gamma-rays included in the integrated count of gamma-rays measured in the main measurement window (MW) is improved.

In other words, the scattered-gamma-ray noise component can be accurately estimated on the basis of count image captured by the gamma camera 1, and removed from the count images. Therefore, the count image becomes clearer.

Second Embodiment

Figure 8:
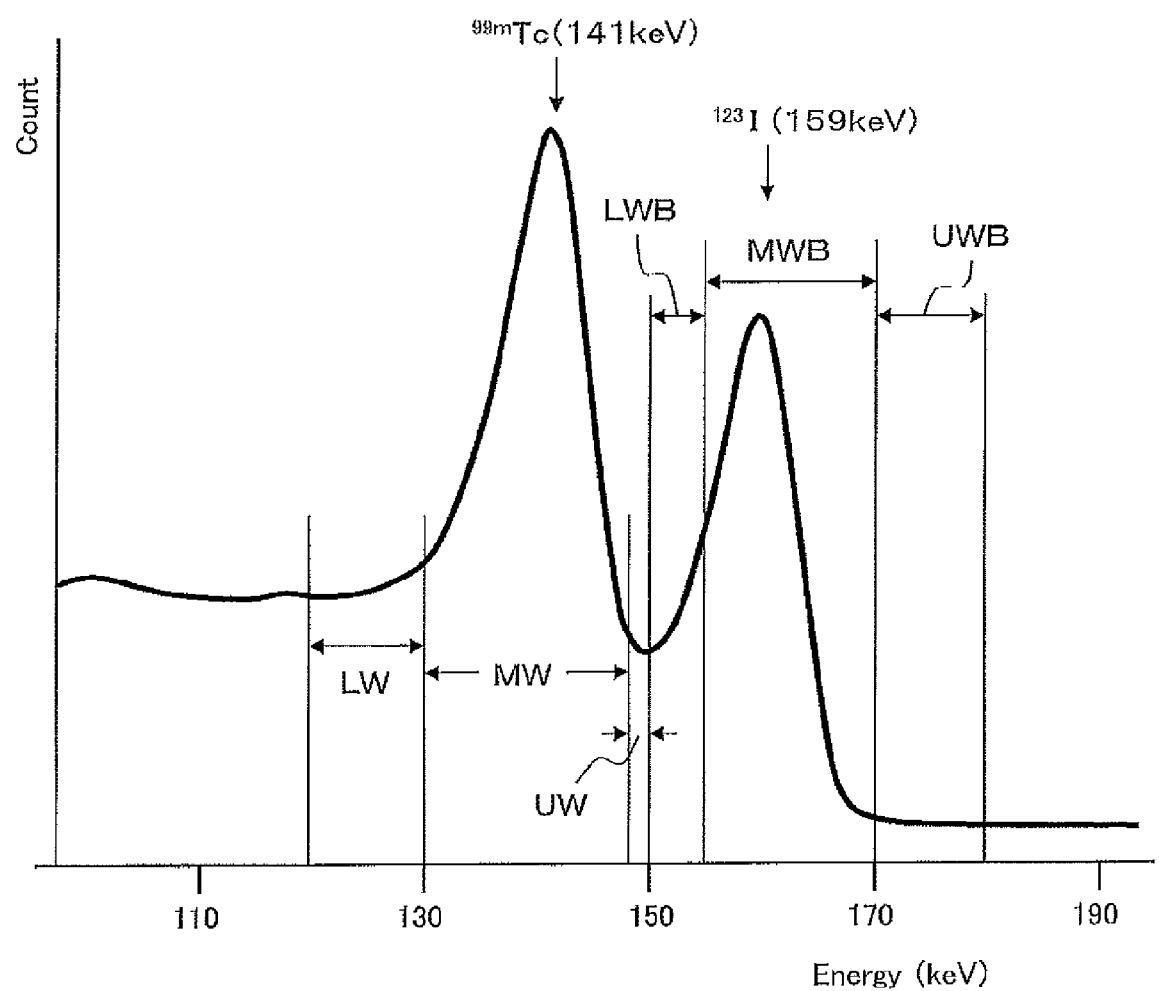
FIG. 8 is a graph illustrating an example of an energy spectrum in simultaneous dual-radionuclide imaging and examples of measurement energy windows which are set for the imaging.

In the second embodiment, a case in which gamma-rays having different energies are measured is explained by taking as an example simultaneous dual-radionuclide imaging of $^{99m}$Tc (141 keV) and $^{123}$I (159 keV, 529 keV). FIG. 8 is a graph indicating an energy spectrum in simultaneous dual-radionuclide imaging and examples of measurement energy windows which are set for the simultaneous dual-radionuclide imaging.

In the case where the gamma-rays 6 emitted from the target objects 5 have a plurality of energy peaks, the number of measurement energy windows which are set varies with the number of energy peaks. In the simultaneous dual-radionuclide imaging according to the present embodiment, as illustrated in FIG. 8, a main measurement energy window (MW: 130 keV to 148 keV), a first subsidiary measurement energy window (LW: 120 keV to 130 keV), and a second subsidiary measurement energy window (UW: 148 keV to 150 keV) are set for $^{99m}$Tc (141 keV), and a main measurement energy window B (MWB: 155 keV to 170 keV), a first subsidiary measurement energy window B (LWB: 150 keV to 155 keV), and a second subsidiary measurement energy window B (UWB: 170 keV to 180 keV) are set for $^{123}$I (159 keV).

In addition, although $^{123}$I also has an energy peak at 529 keV, the energy peak at 529 keV is ignored because the 529 keV peak is not so great and is apart from the energy range used in the present embodiment, and because the explanations on the present embodiment can be simplified. However, the present invention is not limited by the ignorance of the 529 keV peak.

Figure 9:
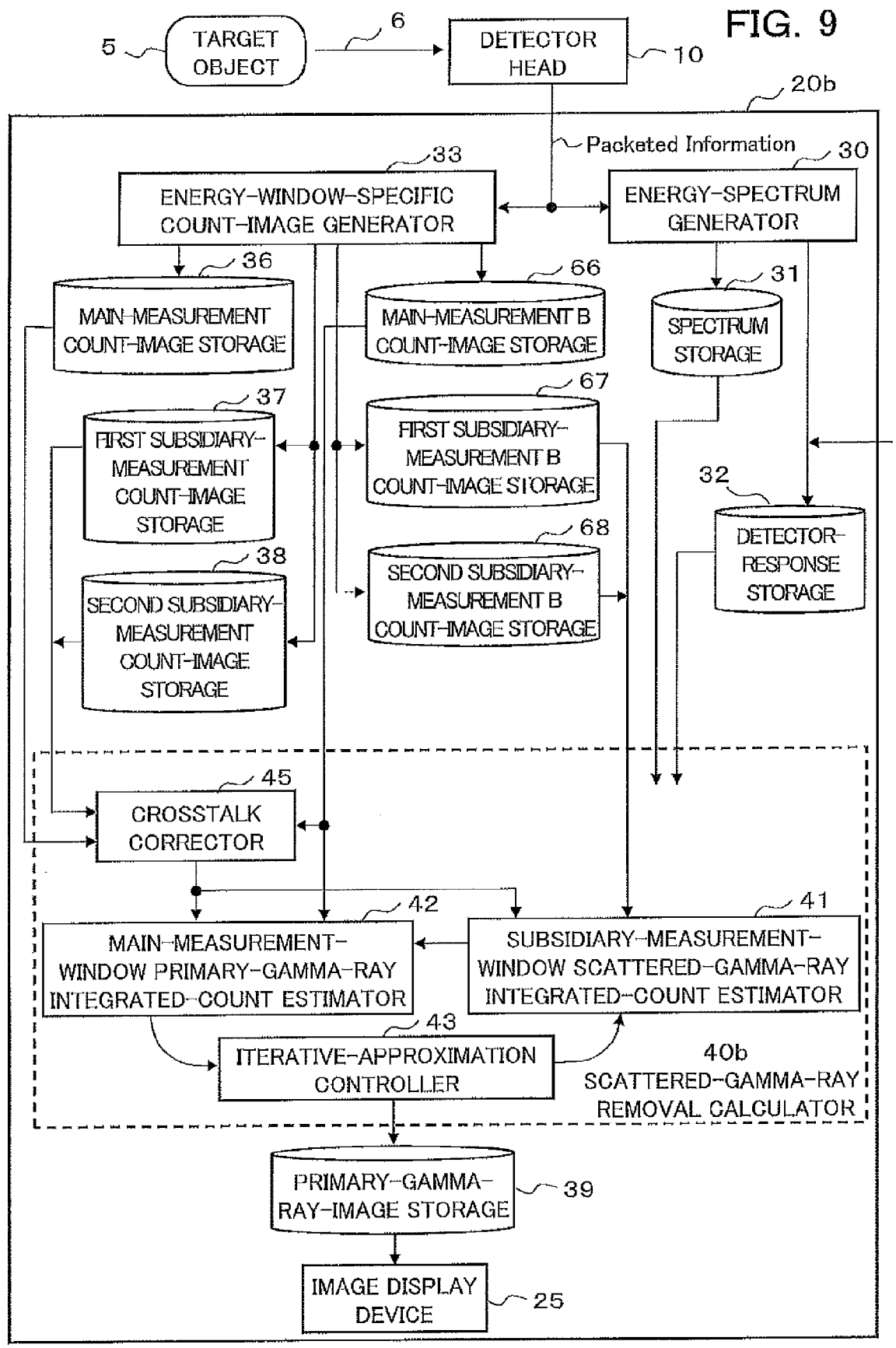
FIG. 9 is a diagram illustrating an example of a function block structure of an information processing device for acquisition of an image of primary gamma-rays in simultaneous dual-radionuclide imaging according to a second embodiment of the present invention.

FIG. 9 is a diagram illustrating an example of a function block structure of an information processing device for acquisition of an image of primary gamma-rays in the simultaneous dual-radionuclide imaging according to the second embodiment of the present invention. As illustrated in FIG. 9, in the function block structure of the information processing device 20b according to the second embodiment, a main-measurement B count-image storage 66, a first subsidiary-measurement B count-image storage 67, and a second subsidiary-measurement B count-image storage 68 are added to the function block structure of the information processing device 20 according to the first embodiment illustrated in FIG. 5. The main-measurement B count-image storage 66, the first subsidiary-measurement B count-image storage 67, and the second subsidiary-measurement B count-image storage 68 store the integrated counts measured in the second main measurement energy window (MWB) and the second subsidiary measurement energy windows (LWB, UWB), respectively.

In addition, as mentioned before, crosstalk occurs in the measured integrated count between gamma-rays having different energies, and the crosstalk causes noise components. Therefore, according to the present embodiment, a crosstalk corrector 45 for correcting the noise components caused by the crosstalk is added to the scattered-gamma-ray removal calculator 40b.

As understood from FIGS. 8 and 2, the measurement energy windows for $^{123}$I are set in the range (150 keV or higher) in which the detector response to $^{99m}$Tc is zero. Therefore, the gamma-rays originally emitted from $^{99m}$Tc do not affect the measurement in the measurement energy windows for $^{123}$I. That is, since gamma-rays originally emitted from $^{123}$I can be handled similarly to the single-radionuclide imaging of $^{123}$I, it is sufficient for the information processing device 20b to perform processing for $^{123}$I similar to the processing by the scattered-gamma-ray removal calculator 40 or 40a in the first embodiment.

On the other hand, since the energies of the gamma-rays originally emitted from $^{123}$I are higher than the measurement energy windows for $^{99m}$Tc, the primary gamma-rays and scattered gamma-rays which are originally emitted from $^{123}$I, as well as the gamma-rays originally emitted from $^{99m}$Tc, are measured in the measurement energy windows for $^{99m}$Tc.

Therefore, as illustrated in FIG. 9, the crosstalk corrector 45 in the information processing device 20b removes from each count image for $^{99m}$Tc the gamma-rays originally emitted from $^{123}$I as much as possible. Specifically, the crosstalk corrector 45 removes influences of the crosstalk with $^{123}$I and the detection energy loss by subtracting from each count image for $^{99m}$Tc the product of the main measurement B count image of $^{123}$I before removal of scattered gamma-rays and the response function ratio of the corresponding measurement energy window.

In addition, although the main measurement B count image of $^{123}$I is used in the above procedure of the crosstalk correction, it is possible to use a combination of the main measurement B count image of $^{123}$I and one or more arbitrary count images of $^{123}$I. A basic concept of crosstalk correction in the above case where a combination of the main measurement B count image of $^{123}$I and one or more arbitrary count images of $^{123}$I is used is explained below with reference to FIG. 10.

Figure 10:
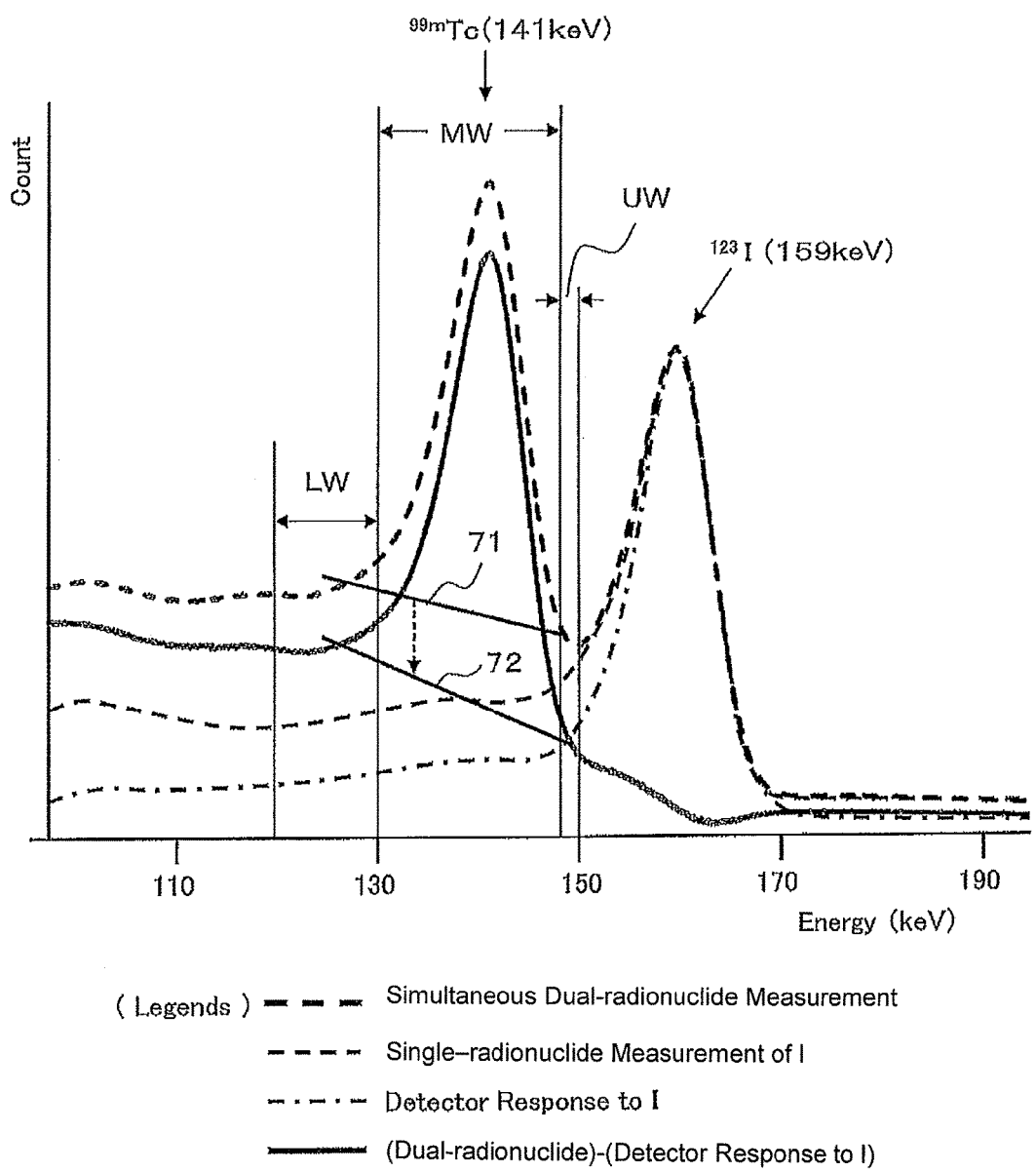
FIG. 10 is a conceptual diagram illustrating operations for crosstalk correction according to the second embodiment of the present invention.

FIG. 10 is a conceptual diagram illustrating operations for crosstalk correction according to the second embodiment of the present invention. In FIG. 10, an energy spectrum in simultaneous dual-radionuclide measurement of a phantom is indicated by the bold dashed curve, an energy spectrum of $^{123}$I in single-radionuclide measurement of the same phantom is indicated by the thin dashed curve, and a detector response to $^{123}$I is indicated by the dash-and-dot curve.

In addition, the data of the simultaneous dual-radionuclide measurement (indicated by the bold dashed curve) minus the detector response to $^{123}$I (indicated by the dash-and-dot curve) is indicated as (Dual-radionuclide)-(Detector Response to I) by the bold solid curve in FIG. 10. Therefore, the amount of (Dual-radionuclide)-(Detector Response to I) can be deemed to correspond to the data of the single-radionuclide measurement of $^{99m}$Tc. That is, the processing for obtaining the amount of (Dual-radionuclide)-(Detector Response to I) is the conceptual representation of the processing performed by the crosstalk corrector 45.

Thus, the components of the detector response to $^{123}$I which are included in the subsidiary measurement energy windows (LW, UW) for $^{99m}$Tc are removed by the processing by the crosstalk corrector 45 as explained above. Therefore, the scattered-gamma-ray noise estimation line in the main measurement energy window (MW) for $^{99m}$Tc is updated from the position of the straight line 71 to the position of the straight line 72. That is, the main-measurement count image and the first and second subsidiary-measurement count images for $^{99m}$Tc in which the crosstalk with $^{123}$I is corrected are obtained by the processing by the crosstalk corrector 45.

Figure 11:
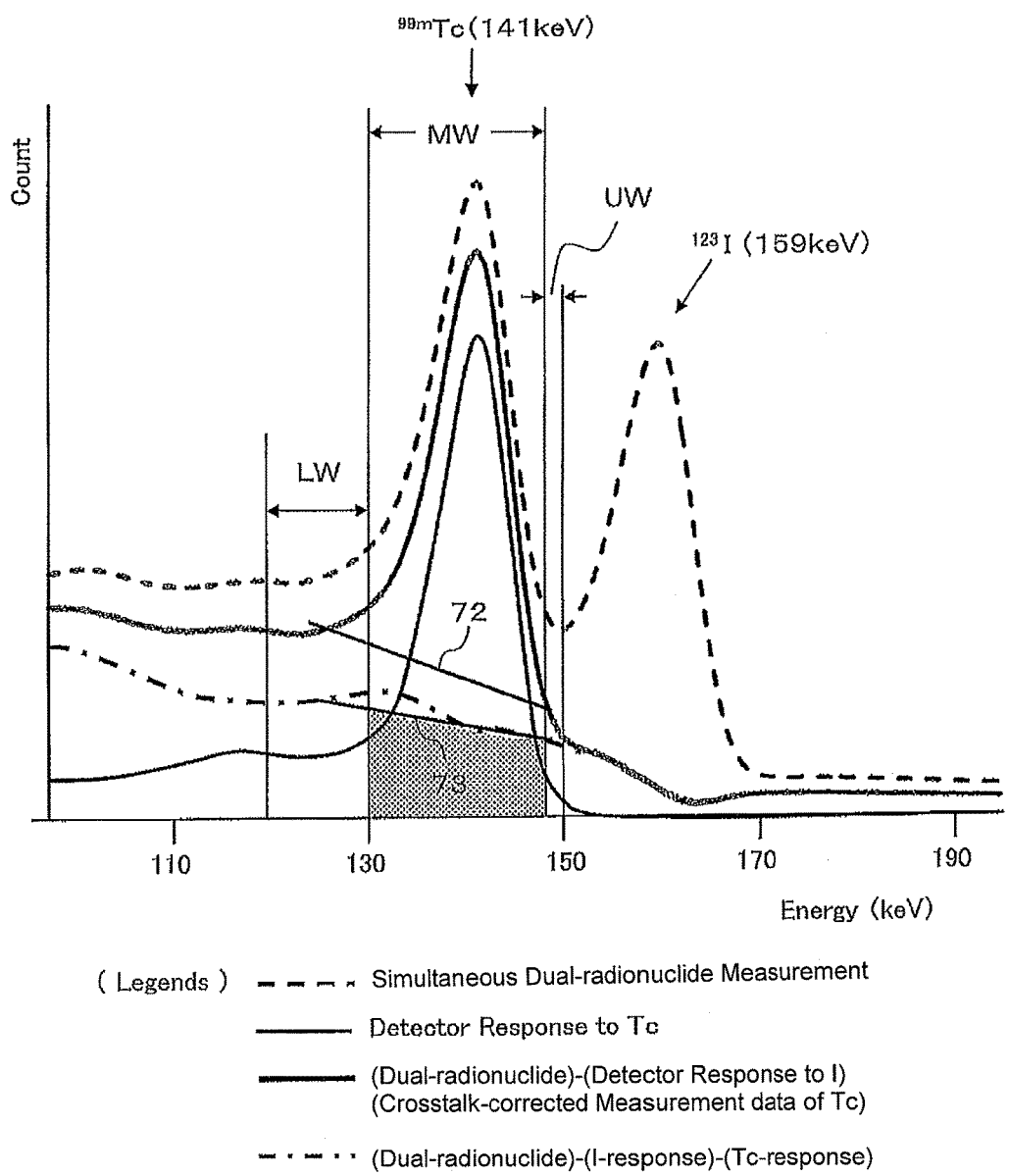
FIG. 11 is a diagram illustrating operations of applying the TEW-DRC technique, where the amount of (Dual-radionuclide)-(Detector Response to I) is assumed to be single-radionuclide measurement data.

Therefore, the information processing device 20b can remove the scattered gamma-rays included in the main measurement count image of $^{99m}$Tc as illustrated in FIG. 11 by regarding the above measurement images as measurement data of only $^{99m}$Tc in the MW, LW, and UW, and applying the TEW-DRC technique explained in the first embodiment.

FIG. 11 is a diagram illustrating operations of applying the TEW-DRC technique, where the amount of (Dual-radionuclide)-(Detector Response to I) is assumed to be single-radionuclide measurement data of $^{99m}$Tc. In FIG. 11, similarly to FIG. 10, an energy spectrum in simultaneous dual-radionuclide measurement is indicated by the bold dashed curve, and the amount of (Dual-radionuclide)-(Detector Response to I) is indicated by the bold solid curve. In addition, a detector response to Tc is indicated by the thin solid curve. Further, the amount of (Dual-radionuclide)-(Detector Response to I) minus the detector response to Tc (i.e., (Dual-radionuclide)-(I-response)-(Tc-response)) is indicated by the dash-and-dot curve.

Since the amount of (Dual-radionuclide)-(Detector Response to I), which is equivalent to crosstalk-corrected measurement data of Tc, is obtained by the processing by the crosstalk corrector 45 (which is explained with reference to FIG. 10), the information processing device 20b can set the main measurement energy window (MW) and subsidiary measurement energy windows (LW, UW) on the amount of (Dual-radionuclide)-(Detector Response to I), and apply the TEW-DRC technique. Resultantly, as illustrated in FIG. 11, the scattered-gamma-ray noise estimation line in the main measurement energy window (MW) for $^{99m}$Tc is updated from the position of the straight line 72 to the position of the straight line 73. That is, a portion of the gamma-ray integrated count of $^{99m}$Tc included in the MW corresponding to the area of the hatched trapezoid under the straight line 73 is removed as the amount of scattered-gamma-ray noise.

As explained above, according to the second embodiment, primary gamma-ray images for a plurality of energies in which the crosstalk noise (including energy loss) and scattered-gamma-ray noise are removed can be obtained in measurement of gamma-rays having a plurality of different energy peaks. Therefore, noise components including the crosstalk noise, energy loss, and the like, as well as the scattered-gamma-ray noise, are appropriately removed from the measurement images taken by the gamma camera 1, so that the measurement images become clearer.

Third Embodiment

Figure 12:
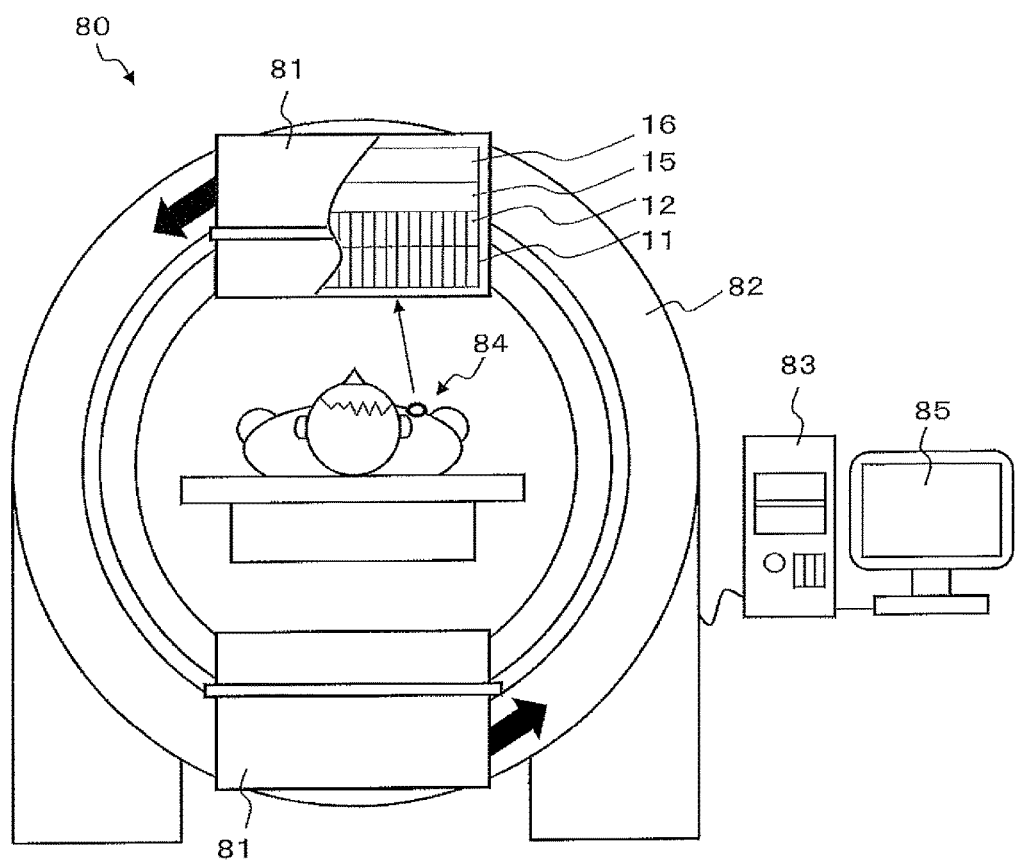
FIG. 12 is a diagram illustrating an outline of an exemplary structure of a SPECT device.

FIG. 12 is a diagram illustrating an outline of an exemplary structure of a SPECT device. As illustrated in FIG. 12, the SPECT device 80 is constituted by one or more detector heads 81, a gantry 82, and a control computer 83. The detector heads 81 are mounted on the gantry 82, and the gantry 82 rotates around a subject 84. The control computer 83 reconstructs a tomographic image of the subject 84 by using count images of the subject 84 which are taken from a plurality of directions by the one or more detector heads 81 rotating around the subject 84.

The one or more detector heads 81 can use the detector head 10 in the gamma camera 1 according to the first embodiment. Therefore, the one or more detector heads 81 are one or more pixel-type gamma-ray detectors having a structure similar to the detector head illustrated in FIG. 3, and are constituted by a collimator 11, semiconductor gamma-ray detectors 12, a signal amplifier 15, a packet-information generation device 16, and other devices. The semiconductor gamma-ray detectors 12 are formed of, for example, cadmium telluride (CdTe) or the like.

The one or more detector heads 81 mounted on the gantry 82 can freely rotationally move along the gantry 82 having a circular shape. Although the rotation angles of the one or more detector heads 81 can be arbitrarily set, the one or more detector heads 81 are generally configured to be able to rotate 180 or 360 degrees around the subject 84. In addition, the one or more detector heads 81 are also configured to be movable in the radial direction of the gantry 82, so that the distance from the subject 84 can be set as needed.

Although not shown, the gantry 82 is provided with a detector-head-position measuring device, which acquires the rotation angles and rotation radii (the distance from the subject 84) of the one or more detector heads 81. Information on the rotation angles and rotation radii of the one or more detector heads 81, which is acquired by the detector-head-position measuring device, is transmitted to the control computer 83 through the packet-information generation device 16.

The control computer 83 has a function block structure similar to one of the information processing devices 20, 20a, and 20b (illustrated in FIGS. 5, 7, and 9) according to the first and second embodiments, and further includes a tomographic-image reconstructor (not shown) which performs processing for reconstructing a tomographic image of the subject 84.

In the control computer 83, the energy-window-specific count-image generator 33 (illustrated in FIG. 5) generates as needed a count image in each measurement energy window according to the energy spectra of gamma-rays radiated from the subject 84. In the SPECT device 80, the count image in each measurement energy window is separately generated at each position (rotation angle and rotation diameter) of the one or more detector heads 81.

In addition, the record format of the count image generated as above may be, for example, the measurement data recording format which is called the sinogram and is generally used with SPECT devices 80. The sinogram is a measurement data recording format which is edited for each LOR (Line of Response), which is determined by a combination of the rotation angle and rotation diameter of each detector head 81.

The count image obtained as above in each measurement energy window at each position of the one or more detector heads 81 is processed by the scattered-gamma-ray removal calculator 40, 40a, or 40b into a primary-gamma-ray image in which the noise component caused by scattered gamma-rays is removed. The primary-gamma-ray image is temporarily stored in the primary-gamma-ray-image storage 39. Subsequently, the control computer 83 performs the processing corresponding to the tomographic-image reconstructor (not shown), so that the primary-gamma-ray images taken from a plurality of positions are transformed into a tomographic image, which is displayed on an image display device 85.

In addition, in the present embodiment, the images of the subject 84 are taken by rotating the one or more detector heads 81. However, Images of the subject 84 may be taken by swinging or translating the one or more detector heads 81. In addition, as mentioned before, according to the present embodiment, the control computer 83 may have a function block structure similar to any of the information processing devices 20, 20a, and 20b (illustrated in FIGS. 5, 7, and 9). Therefore, the SPECT device 80 according to the present embodiment can cope with simultaneous multi-radionuclide imaging of the subject 84.

As explained above, according to the third embodiment, a clearer tomographic image is obtained since the scattered-gamma-ray components are removed from the tomographic image obtained by the SPECT device 80.

Fourth Embodiment

Figure 13:
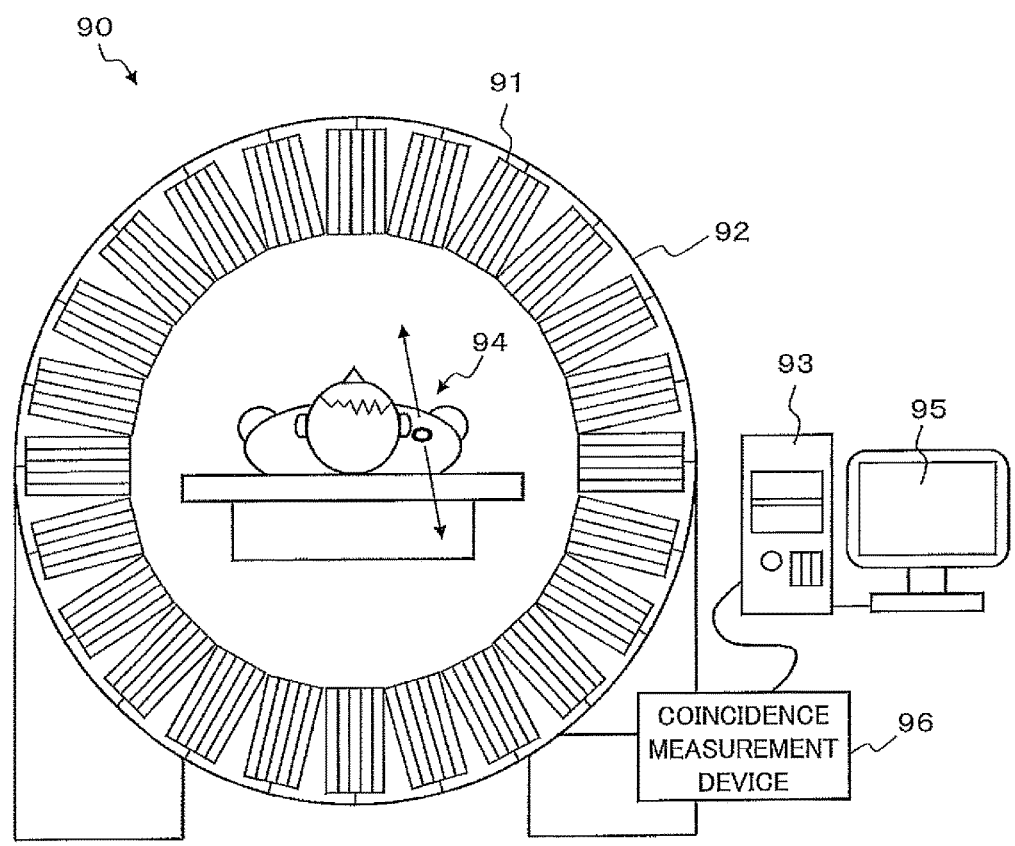
FIG. 13 is a diagram illustrating an outline of an exemplary structure of a PET device.

FIG. 13 is a diagram illustrating an outline of an exemplary structure of a PET device. As illustrated in FIG. 13, the PET device 90 is constituted by a plurality of detector heads 91, a gantry 92, a coincidence measurement device 96, and a control computer 93. The gantry 92 is arranged such that the detector heads 91 encircle 360 degrees around a subject 94. The coincidence measurement device 96 counts coincidences of two gamma-rays detected in a predetermined time window, on the basis of detection signals obtained from the respective detector heads 91. The control computer 93 reconstructs a tomographic image of the subject 94 by using the integrated count of the coincidences of two gamma-rays which is measured by the coincidence measurement device 96.

In the above configuration, an adaptation of the detector head 10 in the gamma camera 1 according to the first embodiment can be used in the detector heads 91. The detector heads 91 are pixel-type gamma-ray detectors. The detector heads 91 may have the same structure as the detector head 10 illustrated in FIG. 3. However, since the collimator 11 is generally unnecessary in the PET device 90, the detector heads 91 in this example each have a structure in which the collimator 11 is removed from the detector head 10.

Therefore, in the present embodiment, the detector heads 91 are each constituted by a semiconductor gamma-ray detector 12, a signal amplifier 15, a packet-information generation device 16, and other devices. In addition, the semiconductor gamma-ray detector 12 is assumed to be formed of, for example, cadmium telluride (CdTe).

When the detection times of gamma-rays included in different information packets inputted from the packet-information generation device 16 are within a predetermined time window, and the LOR (Line of Response) determined on the basis of the combination of the detection positions is within the imaging field, the coincidence measurement device 96 transmits a coincidence count packet as coincidence count information to the control computer 93.

The control computer 93 has a function block structure similar to one of the information processing devices 20 and 20a (illustrated in FIGS. 5 and 7) according to the first embodiment. Since only the positron radionuclide is the target object in the PET device 90, it is unnecessary to consider energy peaks of multiple radionuclides. Therefore, there is no need to consider the structure of the information processing device 20b according to the second embodiment, in which energy peaks of multiple radionuclides, crosstalk, and the like are considered. However, in the case where the SPECT device 80 shares the control computer 93 with the PET device 90, the control computer 93 is required to include the structure of the information processing device 20b (illustrated in FIG. 9).

Therefore, in the control computer 93 (the information processing device 20), the energy-window-specific count-image generator 33 (illustrated in FIG. 5) generates an integrated count for each energy window by using the packeted information on the coincidence measurement, which is transmitted from the coincidence measurement device 96. In the PET device 90, a plurality of count images respectively corresponding to measurement energy windows are generated as sinograms, which are measurement-data recording formats edited on an LOR-by-LOR basis, where LOR stands for line of response, and each LOR is determined by a combination of two detectors which count a coincidence.

The count image which is obtained as above for each measurement energy window and each detector head 91 is temporarily stored, as a primary gamma-ray image in which a noise component of scattered gamma-rays is removed, in the primary-gamma-ray-image storage 39 by the processing performed by the scattered-gamma-ray removal calculator 40 or 40a. Subsequently, in the control computer 93, a tomographic-image reconstructor (not shown) performs processing so as to convert the primary gamma-ray images taken by the multiple detector heads 91 into a tomographic image and display the tomographic image on an image display device 95.

As explained above, according to the fourth embodiment, the noise components of scattered gamma-rays are removed from the tomographic image obtained in the PET device 90, to obtain a clearer tomographic image.

LIST OF REFERENCE SIGNS

1: Gamma Camera
5: Object To Be Measured
6: Gamma Ray
10, 10a: Detector Head
11: Collimator
12: Semiconductor Gamma-ray Detector
13: Scintillator
14: Photodetector
15: Signal Amplifier
16: Packet-information Generation Device
17: Communication Cable
20, 20a, 20b: Information Processing Device
25: Image Display Device
30: Energy-spectrum Generator
31: Spectrum Storage
32: Detector-response Storage
33: Energy-window-specific Count-image Generator
36: Main-measurement Count-image Storage
37: First Subsidiary-measurement Count-image Storage
38: Second Subsidiary-measurement Count-image Storage
39: primary Gamma-ray-image Storage
40, 40a, 40b: Scattered-gamma-ray Removal Calculator
41: Subsidiary-measurement-window Scattered-gamma-ray Integrated-count Estimator
42: Main-measurement-window Primary-gamma-ray Integrated-count Estimator
43: Iterative-approximation Controller
44: Analytic Solution Arithmetic Logic
45: Crosstalk Corrector
66: Main-measurement B Count-image Storage
67: First Subsidiary-measurement B Count-image Storage
68: Second Subsidiary-measurement B Count-image Storage
80: SPECT Device
81: Detector Head
82: Gantry
83: Control Computer
84: Subject
85: Image Display Device
90: PET Device
91: Detector Head
92: Gantry
93: Control Computer
94: Subject
95: Image Display Device
96: Coincidence Measurement Device

The invention claimed is:

1. A gamma camera, comprising:
a pixel-type gamma-ray detector; and
an information processing device including,
    a storage device which stores in advance, as detector-response data, energy spectra which are obtained when gamma-rays emitted from one or more objects to be measured are incident without being scattered, and
    an image display device; wherein
the information processing device includes,
    a first processor which generates a main-measurement count image and a subsidiary-measurement count image on the basis of integrated counts which are respectively measured by a main measurement energy window and a subsidiary measurement energy window, where the main measurement energy window is set for gamma-rays emitted from an object to be measured, and the subsidiary measurement energy window is different from the main measurement energy window,
    a second processor which estimates an integrated count of primary gamma-rays included in the subsidiary measurement energy window on the basis of the detector-response data and the main-measurement count image, and estimates an integrated count of scattered gamma-rays included in the subsidiary-measurement count image by subtracting the estimated integrated count of primary gamma-rays included in the subsidiary measurement energy window from the subsidiary-measurement count image,
    a third processor which estimates an integrated count of primary gamma-rays included in the main measurement energy window, on the basis of the integrated count of scattered gamma-rays included in the subsidiary measurement energy window, which is estimated by the second processor, and a fourth processor which generates a gamma-ray measurement image on the basis of the integrated count of primary gamma-rays estimated by the third processing, and displays the gamma-ray measurement image on the image display device.

2. The gamma camera according to claim 1, wherein in the case where the gamma-rays emitted from the object to be measured include first gamma-rays having a first peak energy and second gamma-rays having a second peak energy lower than the first peak energy, and the information processing device generates a gamma-ray measurement image of the second gamma-rays, the information processing device performs the operations of the second to fourth processors, after performing the operation of the first processor, by regarding, as the main-measurement count image and the subsidiary-measurement count image generated by the first processor, values obtained by subtracting, from the main-measurement count image and the subsidiary-measurement count image generated by the first processor, integrated counts corresponding to the main measurement energy window and the subsidiary measurement energy window which are obtained from the detector-response data stored for the first gamma-rays in the storage device.

3. A gamma camera, comprising:
a pixel-type gamma-ray detector; and
an information processing device including,
  a storage device which stores in advance, as detector-response data, energy spectra which are obtained when gamma-rays emitted from one or more objects to be measured are incident without being scattered, and
  an image display device; wherein
the information processing device includes,
  a first processor which generates a main-measurement count image and a subsidiary-measurement count image on the basis of integrated counts which are respectively measured by a main measurement energy window and a subsidiary measurement energy window, where the main measurement energy window is set for gamma-rays emitted from an object to be measured, and the subsidiary measurement energy window is different from the main measurement energy window,
  a second processor which calculates, as a detector response ratio, a ratio of an integrated count included in the main measurement energy window to an integrated count included in the subsidiary measurement energy window, in the detector-response data stored in the storage device,
  a third processor which estimates an integrated count of scattered gamma-rays included in the subsidiary-measurement count image,
  a fourth processor which estimates an integrated count of primary gamma-rays included in the main-measurement count image,
  a fifth processor which determines whether or not the integrated count of primary gamma-rays estimated by the fourth processor converges, and makes the operations of the third processor and the fourth processor repeatedly performed until the integrated count of primary gamma-rays estimated by the fourth processor is determined to converge, and
  a sixth processor which generates a gamma-ray measurement image based on the integrated count of primary gamma-rays estimated by the fifth processor, and displays the gamma-ray measurement image on the image display device, when convergence is determined by the fifth processor;
wherein in an initial cycle in the repeatedly performed operations, the third processor estimates, as an integrated count of scattered gamma-rays included in the subsidiary-measurement count image, a value obtained by subtracting a product of the detector response ratio and the main-measurement count image, from the subsidiary-measurement count image obtained by the first processing,
in following cycles in the repeatedly performed operations, the third processor estimates, as the integrated count of scattered gamma-rays included in the subsidiary-measurement count image, a value obtained by subtracting a product of the detector response ratio and the integrated count of primary gamma-rays included in the main-measurement count image from the subsidiary-measurement count image obtained by the first processor, which is estimated by the fourth processor, and
the fourth processor estimates an integrated count of scattered gamma-rays included in the main-measurement count image on the basis of the integrated count of scattered gamma-rays included in the subsidiary-measurement count image which is estimated by the third processor, and estimates an integrated count of primary gamma-rays included in the main-measurement count image by subtracting the estimated integrated count of scattered gamma-rays included in the main-measurement count image from the subsidiary-measurement count image obtained by the first processor.

4. The gamma camera according to claim 3, wherein in the case where the gamma-rays emitted from the object to be measured include first gamma-rays having a first peak energy and second gamma-rays having a second peak energy lower than the first peak energy, and the information processing device generates a gamma-ray measurement image of the second gamma-rays, the information processing device performs the operations of the second to sixth processors, after performing the operation of the first processor, by regarding, as the main-measurement count image and the subsidiary-measurement count image generated by the first processor, a value obtained by subtracting, from the main-measurement count image and the subsidiary-measurement count image generated by the first processor, integrated counts corresponding to the main measurement energy window and the subsidiary measurement energy window which are obtained from the detector-response data stored for the first gamma-rays in the storage device.

5. A SPECT device in which the gamma camera according to claim 1 is installed.

6. A PET device in which the gamma camera according to claim 1 is installed.

7. A method for generating a gamma-ray measurement image, executed in a gamma camera which includes,
a pixel-type gamma-ray detector; and
an information processing device including,
  a storage device which stores in advance, as detector-response data, energy spectra which are obtained when gamma-rays emitted from one or more objects to be measured are incident without being scattered, and
  an image display device; wherein
the information processing device performs:
  a first step of generating a main-measurement count image and a subsidiary-measurement count image on the basis of integrated counts which are respectively measured by a main measurement energy window and a subsidiary measurement energy window, where the main measurement energy window is set for gamma-rays emitted from an object to be measured, and the subsidiary measurement energy window is different from the main measurement energy window;

a second step of estimating an integrated count of scattered gamma-rays included in the subsidiary-measurement count image, by estimating an integrated count of primary gamma-rays included in the subsidiary measurement energy window on the basis of the detector-response data and the main-measurement count image, and subtracting the estimated integrated count of primary gamma-rays included in the subsidiary measurement energy window from the subsidiary-measurement count image;

a third step of estimating an integrated count of primary gamma-rays included in the main measurement energy window, on the basis of the integrated count of scattered gamma-rays included in the subsidiary measurement energy window, which is estimated in the second step; and a fourth step of generating a gamma-ray measurement image on the basis of the integrated count of primary gamma-rays estimated by the third step, and displaying the gamma-ray measurement image on the image display device.

8. The method according to claim 7, wherein in the case where the gamma-rays emitted from the object to be measured include first gamma-rays having a first peak energy and second gamma-rays having a second peak energy lower than the first peak energy, and the information processing device generates a gamma-ray measurement image of the second gamma-rays, the information processing device performs the second to fourth steps, after performing the first step, by regarding, as the main-measurement count image and the subsidiary-measurement count image generated in the first step, values obtained by subtracting, from the main-measurement count image and the subsidiary-measurement count image generated by the first step, integrated counts corresponding to the main measurement energy window and the subsidiary measurement energy window which are obtained from the detector-response data stored for the first gamma-rays in the storage device.

9. A method for generating a gamma-ray measurement image, executed in a gamma camera which includes,
a pixel-type gamma-ray detector; and
an information processing device including,
  a storage device which stores in advance, as detector-response data, energy spectra which are obtained when gamma-rays emitted from one or more objects to be measured are incident without being scattered, and
  an image display device; wherein
the information processing device performs:
  a first step of generating a main-measurement count image and a subsidiary-measurement count image on the basis of integrated counts which are respectively measured by a main measurement energy window and a subsidiary measurement energy window, where the main measurement energy window is set for gamma-rays emitted from an object to be measured, and the subsidiary measurement energy window is different from the main measurement energy window;

a second step of calculating, as a detector response ratio, a ratio of an integrated count included in the main measurement energy window to an integrated count included in the subsidiary measurement energy window, in the detector-response data stored in the storage device;

a third step of estimating an integrated count of scattered gamma-rays included in the subsidiary-measurement count image;

a fourth step of estimating an integrated count of primary gamma-rays included in the main-measurement count image;

a fifth step of determining whether or not the integrated count of primary gamma-rays estimated in the fourth step converges, and making operations in the third step and the fourth step repeatedly performed until the integrated count of primary gamma-rays estimated in the fourth step is determined to converge; and a sixth step of generating a gamma-ray measurement image based on the integrated count of primary gamma-rays estimated in the fifth step, and displaying the gamma-ray measurement image on the image display device, when convergence is determined in the fifth step;

wherein in the third step in an initial cycle in the repeatedly performed operations, a value obtained by subtracting a product of the detector response ratio and the main-measurement count image from the subsidiary-measurement count image obtained in the first step is estimated as an integrated count of scattered gamma-rays included in the subsidiary-measurement count image, in the third step in following cycles in the repeatedly performed operations, a value obtained by subtracting a product of the detector response ratio and the integrated count of primary gamma-rays included in the main-measurement count image, which is estimated in the fourth step, from the subsidiary-measurement count image obtained in the first step is estimated as the integrated count of scattered gamma-rays included in the subsidiary-measurement count image, and in the fourth step, an integrated count of scattered gamma-rays included in the main-measurement count image is estimated on the basis of the integrated count of scattered gamma-rays included in the subsidiary-measurement count image which is estimated in the third step, and an integrated count of primary gamma-rays included in the main-measurement count image is estimated by subtracting the estimated integrated count of scattered gamma-rays included in the main-measurement count image from the subsidiary-measurement count image obtained in the first step.

10. The method according to claim 9, wherein in the case where the gamma-rays emitted from the object to be measured include first gamma-rays having a first peak energy and second gamma-rays having a second peak energy lower than the first peak energy, and the information processing device generates a gamma-ray measurement image of the second gamma-rays, the information processing device performs the second to sixth steps, after performing the first step, by regarding, as the main-measurement count image and the subsidiary-measurement count image generated in the first step, values obtained by subtracting, from the main-measurement count image and the subsidiary-measurement count image generated by the first step, integrated counts corresponding to the main measurement energy window and the subsidiary measurement energy window which are obtained from the detector-response data stored for the first gamma-rays in the storage device.

* * * * *